(12) United States Patent
Rosenberg et al.

(10) Patent No.: US 10,293,033 B2
(45) Date of Patent: *May 21, 2019

(54) PROTEOLYTIC EXTRACT FROM BROMELAIN FOR THE TREATMENT OF CONNECTIVE TISSUE DISORDERS

(71) Applicant: MEDIWOUND LTD., Yavne (IL)

(72) Inventors: Lior Rosenberg, Omer (IL); Guy Rubin, Lower Galilee (IL); Eilon Asculai, Lehavim (IL)

(73) Assignee: MediWound Ltd., Yavne (IL)

( * ) Notice: Subject to any disclaimer, the term of this patent is extended or adjusted under 35 U.S.C. 154(b) by 47 days.

This patent is subject to a terminal disclaimer.

(21) Appl. No.: 15/345,482

(22) Filed: Nov. 7, 2016

(65) Prior Publication Data

US 2017/0049865 A1 Feb. 23, 2017

Related U.S. Application Data

(63) Continuation of application No. 14/233,082, filed as application No. PCT/IL2012/050261 on Jul. 19, 2012, now Pat. No. 9,511,126.

(60) Provisional application No. 61/509,612, filed on Jul. 20, 2011.

(51) Int. Cl.
| | |
|---|---|
| A61K 38/48 | (2006.01) |
| A61K 45/06 | (2006.01) |
| A61K 9/00 | (2006.01) |
| A61K 9/08 | (2006.01) |
| A61K 9/14 | (2006.01) |
| A61K 38/17 | (2006.01) |
| A61K 36/88 | (2006.01) |

(52) U.S. Cl.
CPC ........ *A61K 38/4873* (2013.01); *A61K 9/0019* (2013.01); *A61K 9/08* (2013.01); *A61K 9/14* (2013.01); *A61K 36/88* (2013.01); *A61K 38/1732* (2013.01); *A61K 45/06* (2013.01); *C12Y 304/22031* (2013.01); *C12Y 304/22032* (2013.01)

(58) Field of Classification Search
None
See application file for complete search history.

(56) References Cited

U.S. PATENT DOCUMENTS

| | | | |
|---|---|---|---|
| 4,197,291 | A | 4/1980 | Klein et al. |
| 5,106,621 | A | 4/1992 | Rowan et al. |
| 5,589,171 | A | 12/1996 | Wegman |
| 5,830,739 | A | 11/1998 | Houck et al. |
| 6,022,539 | A | 2/2000 | Wegman |
| 6,031,005 | A | 2/2000 | Easterling |
| 6,086,872 | A | 7/2000 | Wegman |
| 6,353,028 | B2 | 3/2002 | Easterling |
| RE39,941 | E | 12/2007 | Wegman |
| 7,811,560 | B2 | 10/2010 | Sabatino et al. |
| 2003/0026794 | A1 | 2/2003 | Fein |
| 2005/0186261 | A1 | 8/2005 | Avelar |
| 2006/0240037 | A1* | 10/2006 | Fey ............ A61K 31/198 424/195.15 |
| 2008/0206228 | A1 | 8/2008 | Vaccaro et al. |
| 2011/0045093 | A1 | 2/2011 | Santana |

FOREIGN PATENT DOCUMENTS

| | | |
|---|---|---|
| GB | 2 323 530 A | 9/1998 |
| JP | H04-503071 A | 6/1992 |
| WO | 02/074329 A1 | 9/2002 |
| WO | 2004/037183 A2 | 5/2004 |
| WO | 2005/074913 A2 | 8/2005 |
| WO | 2006/054309 A2 | 5/2006 |
| WO | 2009/137897 A1 | 11/2009 |

OTHER PUBLICATIONS

Wynn, T.A. 2008. Cellular and molecular mechanisms of fibrosis. Journal of Pathology 214(2): 199-210. pages renumbered as NIH Public Access document as 1-20. specif. p. 1.*
Dupuytren Contracture Institute. Neprinol. Datasheet [online]. Jun. 8, 2011. [retrieved on Aug. 8, 2018]. Retrieved from the Internet: <URL: https://web.archive.org/web/20110608021751/https://dupuytrens-contracture.com/dupuytren-contracture-treatment-options/dupuytren-contracture-neprinol-enzyme-therapy/> pp. 1,7.*
Oliveira, A.S. et al. 2003. Cysteine proteases and cystatins. Brazilian Archives of Biology and Technology 46(1): 1-16. specif. pp. 2,3.*
Soderstrom, K.-O. 1987. Lectin binding to collagen strands in histologic tissue sections. Histochemistry 87: 557-560. specif. p. 557.*
FDA.( U.S. Food and Drug Administration). 0.02M Phosphate saline buffer. Datasheet [online] Jan. 2001. [retrieved on Aug. 8, 2008] Retrieved from the internet: <URL: https://www.fda.gov/Food/FoodScienceResearch/LaboratoryMethods/ucm062947.htm>. p. 1.*
Sullivan et al., "Application of exogenous enzymes to beef muscle of high and low-connective tissue," Meat Science, 85(4):730-734 (2010).
Augoff et al., "Gelatinase A Activity in Dupuytren's Disease," J Hand Surg Am, 31(10):1635-1639 (2006).
Badalamente et al., "Enzyme Injection as Nonsurgical Treatment of Dupuytren's Disease," J Hand Surg Am, 25(4):629-636 (2000).
Desai et al., "Collagenase clostridium histolyticum for Dupuytren's contracture," Expert Opin. Biol. Ther., 10(9):1395-1404 (2010).
Dighe et al., "Bromelain A Wonder Supplement: A Review," Pharmacology online, 1:11-18 (2010).
ExPASy. Stem bromelain. Datasheet [online]. SIB.Swiss Institute of Bioinformatics [retrieved on Mar. 8, 2015]. Artimo et al., 2012. ExPASy: SIB bioinformatics resource portal. Nucleic Acids Research 40(W1): W597-W603. Retrieved from the Internet: URL: http://enzyme.expasy.org/cgi-bin/enzyme/enzyme-search-ec, p. 1.

(Continued)

*Primary Examiner* — Renee Claytor
*Assistant Examiner* — Sharon M. Papciak
(74) *Attorney, Agent, or Firm* — Winston & Strawn LLP

(57) ABSTRACT

The present invention relates to a proteolytic extract obtained from bromelain for the treatment of connective tissue diseases. In particular, the present invention relates to a pharmaceutical composition comprising a proteolytic extract obtained from bromelain for the treatment of diseases such as Dupuytren's disease and Peyronie's disease.

17 Claims, 9 Drawing Sheets

(56) References Cited

OTHER PUBLICATIONS

ExPASy. Ananain. Datasheet [online]. SIB.Swiss Institute of Bioinformatics [retrieved on Aug. 26, 2015]. Artimo et al., 2012. ExPASy: SIB bioinformatics resource portal. Nucleic Acids Research 40(W1): W597-W603. Retrieved from the Internet: URL: http://enzyme.expasy.org/cgi-bin/enzyme/enzyme-search-ec, p. 1.
Fitzhugh et al., "Bromelain Treatment Decreases Neutrophil Migration to Sites of Inflammation," Clin Immunol., 128(1):66-74 (2008).
Gaby, "Natural Remedies for Scleroderma," Alternative Medicine Review, 11(3):188-95 (2006).
Gudmundsson et al., "Eighteen years follow-up study of the clinical manifestations and progression of Dupuytren's disease," Scand J Rheumatol, 30(1):31-34 (2001).
Hale et al., "Proteinase activity and stability of natural bromelain preparations," International Immunopharmacology, 5(4)783-793 (2005).
Holzer et al., "Injectable Collagenase Clostridium Histolyticum for Dupuytren's Contracture," N Engl J Med, 361(26):2579 (2009).
Hurst et al., "Injectable Collagenase Clostridium Histolyticum for Dupuytren's Contracture," N Engl J Med, 361(10):968-979 (2009).
Ketnawa et al., "Two phase partitioning and collagen hydrolysis of bromelain from pineapple peel Nang Lae cultivar," Biochemical Engineering Journal, 52(2-3):205-211 (2010).
Klein et al., "Short-Term Treatment of Painful Osteoarthritis of the Knee with Oral Enzymes: A Randomised, Double-Blind Study versus Diclofenac," Clinical Drug Investigation, 19(1):15-23 (2000).
Lorand et al., "Lens transglutaminase and cataract formation," Proc Natl Acad Sci USA, 78(3):1356-1360 (1981).
Li et al., "Introduction to Bromelain," Food and Drug, 9(01A):26-28 (2007). English Abstract.
Mansell et al., "Abnormal Cancellous Bone Collagen Metabolism in Osteoarthritis," J Clin Invest, 101(8):1596-1603 (1998).
O'Gorman et al., "Molecular mechanisms and treatment strategies for Dupuytren's disease," Therapeutics and Clinical Risk Management, 6:383-390 (2010).
Raval et al., "A database analysis of jacalin-like lectins: sequence-structure-function relationships," Glycobiology, 14(12):1247-1263 (2004).
Rowan et al. "Ananain: A Novel Cysteine Proteinase Found in Pineapple Stem," Archives of Biochemistry and Biophysics, 267(1):262-270 (1988).
Rowan et al., "The cysteine proteinases of the pineapple plant," Biochem. J. 266(3):869-875 (1990).
Shih et al., "Scientific understanding and clinical management of Dupuytren disease," Nature Reviews, Rheumatology, 6(12):715-726 (2010).
Singer et al., "Rapid and Selective Enzymatic Debridement of Porcine Comb Burns with Bromelain-Derived Debrase: Acute-Phase Preservation of Noninjured Tissue and Zone of Stasis," J Burn Care Res, 31(2):304-309 (2010).
Starkweather et al., "Collagenase in the Treatment of Dupuytren's Disease: an In Vitro Study," J Hand Surg Am, 21(3):490-495 (1996).
Watt et al., "Collagenase Injection as Nonsurgical Treatment of Dupuytren's Disease: 8-Year Follow-Up," J Hand Surg Am, 35(4):534-539 (2010).
Wolfram et al., "Hypertrophic Scars and Keloids—A Review of Their Pathophysiology, Risk Factors, and Therapeutic Management," Dermatol Surg, 35(2):171-181 (2009).
MedlinePlus Medical Dictionary. Vitamin E. Datasheet (online). Merriam-Webster (retrieved on Mar. 13, 2015). Copyright 2015. Merriam-Webster, Inc. Retrieved from the Internet: URL: http://www.merriam-webster.com/medlineplus/Vitamin%20. p. 1.
U.S. Appl. No. 14/233,082, Non-Final Rejection, dated Mar. 19, 2015.
U.S. Appl. No. 14/233,082, Non-Final Rejection, dated Sep. 2, 2015.
U.S. Appl. No. 14/233,082, Non-Final Rejection, dated Feb. 8, 2016.
U.S. Appl. No. 14/233,082, Notice of Allowance, dated Jul. 27, 2016.
U.S. Appl. No. 14/233,082, Notice of Allowability, dated Aug. 3, 2016.

\* cited by examiner

PROTEOLYTIC EXTRACT FROM BROMELAIN FOR THE TREATMENT OF CONNECTIVE TISSUE DISORDERS

CROSS-REFERENCE TO RELATED APPLICATIONS

This application is a continuation of U.S. patent application Ser. No. 14/233,082 filed on Jan. 15, 2014, which is a 371 filing of International patent application no. PCT/IL2012/050261 filed on Jul. 19, 2012, which claims the benefit of U.S. provisional patent application No. 61/509,612 filed on Jul. 20, 2011, the entire contents of each of which are incorporated herein by reference thereto.

FIELD OF THE INVENTION

The present invention relates to a proteolytic extract obtained from bromelain for the treatment of connective tissue diseases. In particular, the present invention relates to a pharmaceutical composition comprising a proteolytic extract obtained from bromelain for the treatment of diseases such as Dupuytren's disease and Peyronie's disease.

BACKGROUND OF THE INVENTION

Collagen is the main component of the connective tissue and it is mostly found in fibrous tissues such as tendon, ligament and skin. Numerous diseases and conditions are associated with excess collagen deposition, the most common are Dupuytren's disease and Peronei's disease.

Dupuytren's disease (DD) is a connective tissue disorder of abnormal collagen production and deposition in the hand that is commonly characterized by contracture of metacarpophalangeal joints (MCPJs) and proximal interphalangeal joints (PIPJs) in the ring and little fingers. Fibroblast proliferation and differentiation into myofibroblasts with excess collagen deposition at the level of the palmar fascia cause nodule and fibrotic cord formation in the palm and/or digits. The fibrotic cords or nodules can be of varying thicknesses, from 1 millimeter in diameter for the fibrotic cords to nearly 10 millimeters in diameter for the fibrotic nodules. As the disease progresses, cords begin to contract, causing finger flexion-deformities (flexion contractures) which interfere and decrease hand function.

The prevalence of DD increases with age and males are more often affected. Genetic susceptibility, smoking, alcohol, diabetes mellitus, epilepsy and repetitive manual work are thought to be common risk factors for DD. The severity and progress of DD can be classified by the affected degree of digital flexion-contracture.

Surgical fasciectomy is currently the most widely available treatment for DD which provides positive, though temporary outcomes for most patients. However, surgical fasciectomy usually involves common surgical complications (e.g., infection, hematoma, tissue loss) as well as specific complications such as digital nerve damage, loss of fingers, skin flap loss, wound healing problems and postoperative stiffness. In addition, fasciectomy involves a long recovery and does not offer a definitive cure as DD has an extremely high recurrence rate. Minimally invasive procedures using needles or thin blades have been tried; such procedures though cause less complications, increase the recurrence rate. Non surgical interventions have also been developed and include radiotherapy, ultrasound, injection of vitamin A, vitamin E, steroids and interferon-γ.

In vitro studies have demonstrated the ability of collagenase to decrease the tensile modulus and the force needed to rupture Dupuytren's cord tissue, indicating that collagenase may be effective in enzymatic fasciotomy. Clinical studies have recently demonstrated that treatment with *Clostridium histolyticum* collagenase released DD contractures and improved the range of motion in affected joints. An 8-year follow-up of collagenase injection in patients with DD showed that the MCPJ contracture was less severe following the recurrence of the disease, when compared to the initial contracture before applying the collagenase treatment. It has also been shown that Type-III collagen, which is usually absent from normal adult palmar fascia, is abundant in the tissue of patients with DD.

Peyronie's disease is a connective tissue disorder involving the growth of fibrous plaques rich in collagen in the soft tissue of the penis affecting up to 10% of men. Specifically, the fibrous plaques are formed in the tunica albuginea, the thick sheath of tissue surrounding the corpora cavernosa, cause abnormal curvature which is often associated with pain.

Surgery is the only approach to treating Peyronie's disease which appears to have predictably repeatable efficacy. Surgery is usually only indicated in long-term cases where the disease is stabilized and the deformity prevents intercourse and/or causes extreme pain. However, complications can develop from surgery, including a permanent shortening of the penis.

Non-surgical approaches to Peyronie's disease treatment are also available, although they are all largely ineffective. Attempts to dissolve the plaques by direct intra-lesional injections have been tried. Of the injection methodologies, those involving clostridial collagenase appear to exhibit the most consistent efficacy, though still quite limited in effect and duration. In addition, radiation therapy and laser technology have been tried.

U.S. Pat. Nos. 5,589,171, 6,086,872 and Reissued U.S. Pat. No. RE39,941 disclose methods of treating an individual suffering from Dupuytren's disease which methods comprise applying collagenase to a fibrous affected palmar fascia.

U.S. Pat. No. 6,022,539 discloses methods of treating an individual suffering from Peyronie's disease which methods comprise injecting collagenase into a fibrous Peyronie's plaque in the penis of the individual.

U.S. Pat. No. 6,353,028 discloses topical medicament which comprises calcium channel blocker agents and carrier agents facilitating transdermal delivery of the calcium channel blocker for the treatment of connective tissue disorders: Peyronie's disease, Dupuytren's disease and Ledderhose Fibrosis.

U.S. Patent Application Publication No. 2008/0206228 discloses a medicament containing hyaluronic acid or derivatives thereof in association with collagenase for the treatment of various kinds of wounds, burns, pressure sores, vascular ulcers, and diabetic foot ulcers as well as for the treatment of hypertrophic and keloid scars. Treatment of Dupuytren's disease is explicitly disclosed.

International Patent Application Publication No. WO 2004/037183 discloses methods and compositions for treatment of conditions involving fibrosis, among which Peyronie's disease and Dupuytren's disease are disclosed. The compositions comprise a phosphodiesterase (PDE)-4 inhibitor, a PDE-5 inhibitor or a compound that elevates cGMP, to list some.

Use of cell cycle inhibitors, including anti-microtubule agents, antimetabolites, alkylating agents, vinca alkaloids, PDE inhibitors, matrix metalloproteinase including collagenases, for treating a contracture such as Dupuytren's contracture or Peyronie's contracture is disclosed in International Patent Application Publication No. WO 2005/074913.

Nowhere in the background art is it disclosed or suggested that proteolytic enzymes from plant sources are useful for treating connective tissue disorders involving excess collagen deposition.

Extracts derived from the stem of the pineapple plant (Ananas comosus) have been found to selectively remove devitalized tissue. Such extracts, also named bromelain, contain various proteolytic and hydrolytic enzymes.

International Patent Application Publication No. WO 2006/054309 to the applicant of the present invention discloses a debriding composition obtained from bromelain comprising most of the proteolytic enzymes present in bromelain, the proteolytic enzymes having an average molecular weight of 23 kDa. WO 2006/054309 further discloses uses of said debriding composition for debriding non-viable tissues.

There remains an unmet need for improved non-invasive methods for treating connective tissue diseases involving excess collagen deposition.

SUMMARY OF THE INVENTION

The present invention provides a proteolytic extract obtained from bromelain for the treatment of connective tissue diseases. Particularly, the present invention provides a proteolytic extract obtained from bromelain for the treatment of connective tissue diseases which are associated with excess of collagen deposition, including Dupuytren's disease and Peyronie's disease.

It is now disclosed for the first time that a proteolytic extract obtained from bromelain comprising one or more of the cysteine proteases present in bromelain, e.g., stem bromelain or ananain, is capable of degrading native, non-denatured collagen. Unexpectedly, injection of the proteolytic extract into a Dupuytren's cord resulted in rupture of the cord while maintaining the normal healthy connective tissue intact.

The present invention further discloses that the efficacy of the proteolytic extract to rupture or dissolve Dupuytren's cords is similar to or even higher than that of collagenase. However, while collagenase may cause damage to non-diseased ligaments or tendons due to its affinity to the various types of collagen, the proteolytic extract of the present invention shows specificity to the diseased cords. Thus, the proteolytic extract of the present invention provides an improved and safe medication for connective tissue diseases which involve excess collagen deposition, particularly for the treatment of Dupuytren's disease and Peronei's disease.

Due to the fact that high concentrations of the proteolytic extract can be prepared in small volumes, such small volumes can be injected into the diseased fibrous cords or plaques, thus avoiding extravasation and damage to surrounding tissues, simplifying the clinical procedure and hence increasing patient's compliance.

According to one aspect, the present invention provides a method of treating a connective tissue disease comprising administering to a subject in need of such treatment a pharmaceutical composition comprising a therapeutically effective amount of a proteolytic extract obtained from bromelain and a pharmaceutically acceptable carrier, wherein the proteolytic extract comprises at least one cysteine protease selected from the group consisting of stem bromelain and ananain, and wherein the connective tissue disease is associated with excess collagen deposition.

According to additional embodiments, the connective tissue disease is selected from the group consisting of Dupuytren's disease, Peyronie's disease, frozen shoulder, and Ledderhose disease. According to a certain embodiment, the connective tissue disease is Dupuytren's disease. According to another embodiment, the connective tissue disease is Peronei's disease.

According to one embodiment, the proteolytic extract comprises stem bromelain and ananain. According to another embodiment, the proteolytic extract further comprises a cysteine protease precursor. According to a further embodiment, the proteolytic extract further comprises a cysteine protease fragment. According to an exemplary embodiment, the proteolytic extract comprises stem bromelain, ananain, and a cysteine protease precursor.

According to further embodiments, the pharmaceutical composition further comprising an agent selected from the group consisting of an anesthetic agent, antibacterial agent and an anti-inflammatory agent.

According to still further embodiments, the anesthetic agent is selected from the group consisting of amethocaine (tetracaine), lignocaine (lidocaine), xylocaine, bupivacaine, prilocaine, ropivacaine, benzocaine, mepivocaine, cocaine and combinations thereof. Each possibility is a separate embodiment of the invention.

According to additional embodiments, the antibacterial agent is selected from the group consisting of amanfadine hydrochloride, amanfadine sulfate, amikacin, amikacin sulfate, amoglycosides, amoxicillin, ampicillin, amsamycins, bacitracin, beta-lactams, candicidin, capreomycin, carbenicillin, cephalexin, cephaloridine, cephalothin, cefazolin, cephapirin, cephradine, cephaloglycin, chilomphenicols, chlorhexidine, chloshexidine gluconate, chlorhexidine hydrochloride, chloroxine, chlorquiraldol, chlortetracycline, chlortetracycline hydrochloride, ciprofloxacin, circulin, clindamycin, clindamycin hydrochloride, clotrimazole, cloxacillin, demeclocycline, diclosxacillin, diiodohydroxyquin, doxycycline, ethambutol, ethambutol hydrochloride, erythromycin, erythromycin estolate, erhmycin stearate, farnesol, floxacillin, gentamicin, gentamicin sulfate, gramicidin, giseofulvin, haloprogin, haloquinol, hexachlorophene, iminocylcline, iodochlorhydroxyquin, kanamycin, kanamycin sulfate, lincomycin, lineomycin, lineomycin hydrochloride, macrolides, meclocycline, methacycline, methacycline hydrochloride, methenine, methenamine hippurate, methenamine mandelate, methicillin, metonidazole, miconazole, miconazole hydrochloride, minocycline, minocycline hydrochloride, mupirocin, nafcillin, neomycin, neomycin sulfate, netimicin, netilmicin sulfate, nitrofurazone, norfloxacin, nystatin, octopirox, oleandomycin, orcephalosporins, oxacillin, oxyteacline, oxytetracycline hydrochloride, parachlorometa xylenol, paromomycin, paromomycin sulfate, penicillins, penicillin G, penicillin V, pentamidine, pentamidine hydrochloride, phenethicillin, polymyxins, quinolones, streptomycin sulfate, tetracycline, tobramycin, tolnaftate, triclosan, trifampin, rifamycin, rolitetracycline, silver salts, spectinomycin, spiramycin, struptomycin, sulfonamide, tetracyclines, tetracycline, tobramycin, tobramycin sulfate, triclocarbon, triclosan, trimethoprim-sulfamethoxazole, tylosin, vancomycin, and yrothricin. Each possibility is a separate embodiment of the invention.

According to further embodiments, the anti-inflammatory agent is selected from the group consisting of non-steroidal anti-inflammatory agents and steroidal anti-inflammatory agents.

According to yet further embodiments, the pharmaceutical composition further comprises a component selected from the group consisting of a stabilizing agent, an antioxidant, a preservative, a buffering agent, a chelating agent, and a tonicity agent.

According to still further embodiments, the pharmaceutical composition is formulated in a form selected from the group consisting of a solid formulation, a semi solid formulation, a liquid formulation and a foam formulation. According to a certain embodiment, the solid formulation is a powder. According to another embodiment, the liquid formulation is an injectable solution of a pH of about 6 to about 7.

According to an exemplary embodiment, the pharmaceutical composition is administered by injection into the diseased fibrous tissue. The pharmaceutical composition can be injected as a single dose or in aliquots at two or more locations in the diseased fibrous tissue.

According to another aspect, the present invention provides a pharmaceutical composition comprising a proteolytic extract for use in the treatment of a connective tissue disease, wherein the proteolytic extract comprises at least one cysteine protease selected from the group consisting of stem bromelain and ananain, and wherein the connective tissue disease is associated with excess collagen deposition.

These and other embodiments of the present invention will be better understood in relation to the figures, description, examples, and claims that follow.

BRIEF DESCRIPTION OF THE DRAWINGS

FIG. 5A is a photograph showing the abnormal contracture of the ring finger in a patient with Dupuytren's disease. FIG. 5B is a photograph showing the surgical removal of the pathological cord. FIG. 5C is a photograph showing the cord after removal from the palmar bed.

FIG. 10A shows the cord before tensile force application. FIG. 10B shows the cord after tensile force application and before cord rupture.

DETAILED DESCRIPTION OF THE INVENTION

Figure 1:
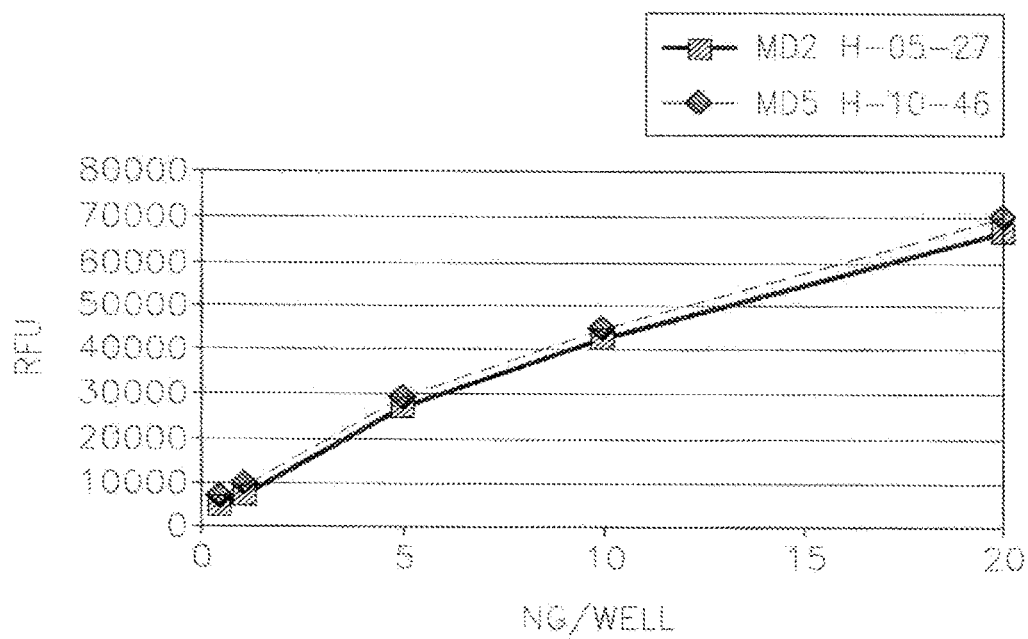
FIG. 1 is a graph showing the collagenolytic activity of two batches of the proteolytic extract. Increasing concentrations of the proteolytic extracts (designated MD2 H-05-27 and MD5 H-10-46) were incubated for 20 minutes in the presence of fluorescently labeled collagen type IV. At the end of the incubation fluorescence was measured. Results are presented in relative fluorescence units (RFU).

The present invention provides methods of treating connective tissue diseases involving excess collagen deposition comprising administering to a subject in need of such treatment a proteolytic extract obtained from bromelain.

A debriding composition obtained from bromelain (also termed Debrase®) was first disclosed in WO 2006/054309 to the applicant of the present invention, the content of which is incorporated by reference as if fully set forth herein. The debriding composition disclosed in WO 2006/054309 comprises cysteine proteases such as stem bromelain and ananain. WO 2006/054309 further discloses that the debriding composition debrided burned skin, i.e., devitalized tissue, more efficiently than bromelain. However, the debriding composition was found to be inactive in debriding healthy or vital skin or dermis (see, for example, Singer et al., 2010, J. Burn Care Res. 31: 304-309). The debriding composition was therefore shown to be active against devitalized tissues, not against viable tissues.

Unexpectedly, the present invention discloses that a proteolytic extract obtained from bromelain exerted collgenolytic activity in vitro and was capable of dissolving the palmar fibrotic cords obtained from subjects suffering from Dupuytren's disease. As the proteolytic extract of the present invention does not degrade healthy connective tissue, the present invention thus provides safe and efficient enzymatic medicament for dissolving fibrous tissue rich in collagen, specifically in subjects suffering from Dupuytren's disease or Peronei's disease.

The terms "proteolytic extract obtained from bromelain" and "proteolytic extract" are used interchangeably throughout the specification and claims and refer to an enzymatic preparation partially purified from bromelain.

The term "bromelain" refers to any of a number of presently commercially available bromelain powder preparations. Examples of manufacturers of bromelain include, but are not limited to, Sigma and Challenge Bioproducts Co. Ltd., Taiwan. Bromelain is prepared from the stem of pineapple plant. A typical procedure to obtain bromelain is as follows: the juice from the stem of pineapple plant is first adjusted to a pH of about 3 or 4 with phosphoric acid, and sodium hydride or sodium sulfhydride is added to protect against sulfhydryl oxidation. The inert material is precipitated at about 30% acetone and, after filtration, the clarified fluid is precipitated with 70% acetone. This precipitate is collected by centrifugation and either redissolved in water containing sodium hydride or sodium sulfhydride which has been acidified with phosphoric acid and reprecipitated, or dried in a vacuum oven directly. If the material is reprecipitated, 70% acetone is utilized. The dried material from either process is suitable as a starting material to obtain the debriding composition of the present invention.

The proteolytic extract of the present invention can comprise one or more of the cysteine proteases present in bromelain. According to an exemplary embodiment, the proteolytic extract (also termed Debrase® or Nexobrid®) comprises the cysteine proteases stem bromelain (EC 3.4.22.32) and ananain (EC 3.4.22.31). The proteolytic extract can further comprise one or more of the cysteine protease precursors of bromelain such as, for example, ananain (EC 3.4.22.31) precursor, fruit bromelain (EC 3.4.22.33) precursor, and stem bromelain (EC 3.4.22.31) precursor. The proteolytic extract can further comprise cysteine protease fragments (see, for example, WO 2006/054309), a jacalin-like lectin (see, for example, Raval et al., Glycobiology, 2004, 14(12): 1247-1263), and/or bromelain inhibitors.

The proteolytic extract can be prepared by a method comprising the following steps:
  (a) suspending bromelain with an acidic solution optionally comprising an anti-oxidant, the acidic solution having a pH in the range from about 2.4 to about 4;
  (b) adjusting the suspension of (a) to a pH in the range from about 2.4 to about 4;
  (c) adding a filter aid to the suspension of (b);
  (d) filtering the suspension of (c) to remove insoluble components;
  (e) adding to the filtered solution of (d) ammonium sulfate salt to yield saturation of ammonium sulfate in the range from about 40% to about 50%;
  (f) adjusting the suspension of (e) to a pH from about 2.5 to about 4;
  (g) incubating the suspension of (f) at 3° C.-10° C.;
  (h) centrifuging the suspension of (g) to yield an ammonium sulfate precipitate;
  (i) dissolving the ammonium sulfate precipitate in an acidic solution optionally comprising an anti-oxidant having a pH in the range from about 2.4 to about 4;
  (j) filtering the solution of (i) through a 10 kDa ultra-filter; and
  (k) lyophilizing the retained solution of (j).

According to some embodiments, suspending bromelain can be performed in any acidic solution having a pH between about 2.4 to 4. Examples of acidic solutions or buffers that can be used according to the present invention include, but are not limited to, acetic acid in water, acetate buffer and acetate buffer containing 1% thioglycolic acid, pH 2.4-4. According to certain exemplary embodiments, the acidic solution is selected from the buffers and solutions disclosed in U.S. Pat. Nos. 5,830,739 and 4,197,291, the content of which is incorporated by reference as if fully set forth herein.

The acidic solution can optionally comprise an anti-oxidant. Examples of anti-oxidants include, but are not limited to, ascorbic acid, dihydroquinon, butylated hydroxytoluene and dithiothreitol. The anti-oxidant can be added at a concentration of about 0.5% to about 2%, preferably at 1%.

The acidic solution can further comprise a wetting agent. Examples of wetting agents include, but are not limited to, n-octanol.

The pH of the acidic solution, which optionally comprises an anti-oxidant, can be in the range from about 2.4 to about 4. According to a certain preferred embodiment, the pH of the acidic solution, which optionally comprises an anti-oxidant, ranges from about 2.4 to about 2.6.

According to additional embodiments, a filter aid is added to the suspension of (a). According to one embodiment, the filter aid comprises silica. Preferably, the filter aid is natural diatomite that is calcined so that faster flow rates are achieved.

Precipitating the desired proteins is performed by adding to the filtered solution of step (d) ammonium sulfate salt. Ammonium sulfate salt can be added to yield saturation of the ammonium sulfate at a range of between about 40% to about 50%. Preferably, ammonium sulfate salt can be added to yield 40% saturation of ammonium sulfate.

The suspension of step (f) is then incubated at a temperature between 3° C. to 10° C. Preferably, the suspension of step (f) is incubated for at least 10 hours at temperatures between 3° C. to 10° C. More preferably, the suspension of step (f) is incubated for 12-24 hours at 4° C.

At the end of the incubation, the suspension of step (g) is centrifuged to precipitate the desired proteins, i.e., the proteolytic enzymes. The precipitate is then dissolved in acidic solution optionally comprising an anti-oxidant. According to an exemplary embodiment, the suspension is incubated for at least 10 hours at 4° C.

The solution of step (i) is subjected to a step of filtering to retain proteolytic enzymes having molecular weights in excess of about 10 kDa. According to a preferred embodiment, the solution of step (i) is filtered through a membrane filter having a molecular weight cut off of about 10 kDa.

The proteolytic extract can be lyophilized after filtration, can be washed with distilled water and then lyophilized or can be filtered and then lyophilized. According to a currently preferred embodiment, the proteolytic extract is filtered through a filter membrane having a pore size of at least about 0.5 μm to obtain a sterile solution, which is then lyophilized and stored. Preferably, the proteolytic extract is stored as a lyophilized powder as its stability is prolonged in the absence of moisture. Prior to use, the proteolytic extract is dissolved in a solution so as to obtain a solution with a pH of about 6 to about 7.

According to an exemplary embodiment, the proteolytic extract can be prepared by the method comprising the following steps:
  (a) suspending bromelain with 0.3 M acetic acid comprising 1% ascorbic acid and n-octanol having a pH from about 2.4 to about 2.6;
  (b) adjusting the suspension of (a) to a pH in the range from about 2.5 to about 3.5;
  (c) adding a filter aid comprising silica to the suspension of (b);

(d) filtering the suspension of (c) through a filter press to remove insoluble components;

(e) adding to the filtered solution of (d) ammonium sulfate salt (285 g/L) to yield 40% saturation of ammonium sulfate;

(f) adjusting the suspension of (e) to a pH from about 2.5 to about 3.5;

(g) incubating the suspension of (f) for approximately 12-24 hours at 4° C.;

(h) centrifuging the suspension of (g) to yield an ammonium sulfate precipitate;

(i) dissolving the ammonium sulfate precipitate in 0.3 M acetic acid comprising 1% ascorbic acid having a pH from about 2.4 to about 2.6;

(j) filtering the solution of (i) through a 10 kDa ultra-filter;

(k) filtering the retained solution of (j) to yield a sterile solution; and (l) lyophilizing the filtered solution of (k).

The term "Dupuytren's disease" and "DD" are interchangeably used herein and refer to a disease where the fingers cannot fully extend and are usually flexed towards the palm of the hand. Specifically, Dupuytren's disease begins with the formation of fibromatous nodules in the palmar fascia, usually in the ulnar side. The nodules progress and form a fibrous band or cord lying from the palm to the fingers. Eventually this leads to permanent finger flexion-contractures. The ring finger is most commonly affected, followed by the little finger.

The terms "Dupuytren's cord" and "the diseased cord" are used herein interchangeably and refer to the bands of fascial fibers that run longitudinally bellow the palmar skin. These bands lead to contractures of the overlay skin and distal digits that are attached to the bands and eventually progresses to permanent flexion-contracture of the affected digits. Typically, the Dupuytren's cord comprises high numbers of fibroblasts, increased deposition of extracellular matrix (ECM) proteins, particularly collagen, and myofibroblasts.

It is to be understood that the proteolytic extract of the invention is useful for treating individuals having other diseases associated with excess collagen deposition. Other fibrous tissue malformations and abnormalities which involve collagen deposition include Peyronie's disease, Ledderhose Fibrosis, and fibrosis of joint-capsules, tendons and ligaments sheaths. Thus, the proteolytic extract can also be useful for treating frozen shoulder (adhesive capsulitis). These connective tissue diseases involving excess collagen deposition or fibrous tissue malformations are not associated with wounds or burns.

As used herein, the terms "treating" or "treatment" refer to amelioration or elimination of at least one or more of the symptoms associated with a connective tissue disease. For example, symptoms associated with Dupuytren's disease include joint contracture, decrease range of motion of the joints, to list some. Symptoms of Peyronie's disease include, for example, pain, abnormal curvature, and erectile dysfunction.

The term "therapeutically effective amount" of the proteolytic extract is that amount of the proteolytic extract which is sufficient to provide a beneficial effect to the subject to which the composition is administered.

The term "about" when refers to a pH of a solution or suspension is meant to indicate that 0.5 pH units above or below the indicated pH are within the scope of the present invention.

The pharmaceutical composition of the present invention comprises the proteolytic extract and a pharmaceutically acceptable carrier.

The term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, excipient, or vehicle with which the proteolytic extract is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Saline solutions, aqueous NaCl/CaCl2 solution, aqueous dextrose, glycerol solutions and albumin solutions can be employed as liquid carriers, particularly for injectable solutions. Water can also be used as a carrier when the pharmaceutical composition is administered intravenously;

The pharmaceutical composition can further comprise stabilizing agents such as lactose, dextrose, sucrose, sorbitol, mannitol, starch, gum acacia, calcium phosphate, alginates, tragacanth, calcium silicate, polyvinylpyrrolidone and cellulose. The composition can additionally include lubricating agents, such as, magnesium stearate and mineral oil; wetting agents; emulsifying and suspending agents; preservatives such as Thimerosal, benzyl alcohol, parabens, methyl- or propylhydroxybenzoates; anti-oxidants such as ascorbic acid, dihydroquinon, butylated hydroxytoluene and dithiothreitol; and buffering agents such as monobasic sodium phosphate, dibasic sodium phosphate, sodium benzoate, potassium benzoate, sodium citrate, sodium acetate, and sodium tartrate; chelating agents such as ethylenediaminetetraacetic acid; and agents for the adjustment of tonicity such as sodium chloride or dextrose.

The pharmaceutical composition can further comprise an anesthetic agent.

Anesthetic agents include, but are not limited to, amethocaine (tetracaine), lignocaine (lidocaine), xylocaine, bupivacaine, prilocaine, ropivacaine, benzocaine, mepivocaine, cocaine and combinations thereof.

The pharmaceutical composition can further comprise an antibacterial agent.

Antibacterial agents include, but are not limited to, amanfadine hydrochloride, amanfadine sulfate, amikacin, amikacin sulfate, amoglycosides, amoxicillin, ampicillin, amsamycins, bacitracin, beta-lactams, candici din, capreomycin, carbenicillin, cephalexin, cephaloridine, cephalothin, cefazolin, cephapirin, cephradine, cephaloglycin, chilomphenicols, chlorhexidine, chloshexidine gluconate, chlorhexidine hydrochloride, chloroxine, chlorquiraldol, chlortetracycline, chlortetracycline hydrochloride, ciprofloxacin, circulin, clindamycin, clindamycin hydrochloride, clotrimazole, cloxacillin, demeclocycline, diclosxacillin, diiodohydroxyquin, doxycycline, ethambutol, ethambutol hydrochloride, erythromycin, erythromycin estolate, erhmycin stearate, farnesol, floxacillin, gentamicin, gentamicin sulfate, gramicidin, giseofulvin, haloprogin, haloquinol, hexachlorophene, iminocylcline, iodochlorhydroxyquin, kanamycin, kanamycin sulfate, lincomycin, lineomycin, lineomycin hydrochloride, macrolides, meclocycline, methacycline, methacycline hydrochloride, methenine, methenamine hippurate, methenamine mandelate, methicillin, metonidazole, miconazole, miconazole hydrochloride, minocycline, minocycline hydrochloride, mupirocin, nafcillin, neomycin, neomycin sulfate, netimicin, netilmicin sulfate, nitrofurazone, norfloxacin, nystatin, octopirox, oleandomycin, orcephalosporins, oxacillin, oxyteacline, oxytetracycline hydrochloride, parachlorometa xylenol, paromomycin, paromomycin sulfate, penicillins, penicillin G, penicillin V, pentamidine, pentamidine hydrochloride, phenethicillin, polymyxins, quinolones, streptomycin sulfate, tetracycline, tobramycin, tolnaftate, triclosan, trifampin, rifamycin, rolitetracycline, silver salts, spectinomycin, spiramycin, struptomycin, sulfonamide, tetracyclines, tetracycline, tobramycin, tobramycin sulfate, triclocarbon, triclosan, trimethoprim-sulfamethoxazole, tylosin, vancomycin, and yrothricin.

According to yet another embodiment, the pharmaceutical composition can further comprise an anti-inflammatory agent.

The anti-inflammatory agent can be non-steroidal, steroidal, or a combination thereof. Non limiting examples of non-steroidal anti-inflammatory agents include, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Extracts of these non-steroidal anti-inflammatory agents may also be employed.

Non-limiting examples of steroidal anti-inflammatory drugs include, corticosteroids such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocorisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and extracts thereof.

The pharmaceutical composition can be formulated as a dry or lyophilized formulation, semi solid formulation, liquid formulation or a foam formulation. Thus, the pharmaceutical composition can be formulated in the form of a powder, solution, suspension, emulsion, gel, spray, or a patch.

The pharmaceutical composition can be administered into the affected site topically, subcutaneously, intracutaneously, or intramuscularly.

According to a certain embodiment, the pharmaceutical composition is administered by injection. According to an exemplary embodiment, the pharmaceutical composition is injected directly into the diseased fibrous nodules or cord or into the fibrous plaque. Alternatively, the pharmaceutical composition is implanted into a surgical incision. Sterile injectable preparations may be formulated as aqueous solutions or oleaginous suspensions as known in the art.

For topical use on the skin the pharmaceutical composition can be formulated in the form of an ointment, cream, lotion, paste, spray, or aerosol. Examples of suitable vehicles include, but are not limited to, petrolatum, aquaphor, neobase, propylene glycol, glycerin and the like. Combinations of two or more of these vehicles can also be used.

The pharmaceutical composition may be formulated as controlled or sustained release formulations allowing for extended release of the active components over a predetermined time period. In a certain embodiment, the pharmaceutical composition is administered in combination with a biodegradable, biocompatible polymeric implant, which releases the proteolytic extract over a controlled period of time at a selected site. Examples of polymeric materials include polyanhydrides, polyorthoesters, polyglycolic acid, polylactic acid, polyethylene vinyl acetate, copolymers and blends thereof (See, Medical applications of controlled release, Langer and Wise (eds.), 1974, CRC Pres., Boca Raton, Fla.). Alternatively, the pharmaceutical composition is applied topically as a gel. Examples of polymeric materials that can be used are polysaccharides, particularly cellulose derivatives such as, for example, hydroxypropyl cellulose, carboxymethyl cellulose, and hydroxyethyl cellulose, chitin, chitosan, and alginates. The gel formulation would allow for extended release of the active components over a predetermined period of time.

The pharmaceutical composition can be formulated as foam. Gas propellants are used to generate and administer a foamable composition as foam. Examples of suitable gas propellants include volatile hydrocarbons such as butane, propane, isobutane or mixtures thereof, and fluorocarbon gases. The composition may be aqueous, oil-in-water emulsion or water-in-oil emulsion, further comprising a stabilizing agent. The stabilizing agent increases the viscosity of the composition, can contribute to the composition stability, and/or slows foam collapse rate. Examples of stabilizing agents include, but are not limited to, naturally-occurring polymeric materials (e.g., alginate, albumin, carrageenan, xanthan gum, starch), semi-synthetic polymeric materials such as cellulose ethers (e.g. hydroxyethyl cellulose, methyl cellulose, carboxymethyl cellulose, hydroxy propylmethyl cellulose), and synthetic polymeric materials (e.g., polyvinyl alcohol, carboxyvinyl polymers, and polyvinylpyrrolidone).

Techniques for formulation and administration of drugs can be found in "Remington's Pharmaceutical Sciences," Mack Publishing Co., Easton, Pa., latest edition, which is incorporated herein by reference.

The pharmaceutical composition can be administered as a single dose, or in aliquots at two or more locations in the affected fibrous tissue. The amount of the proteolytic extract to be administered is an effective amount which softens and/or ruptures the plaque. An effective amount of the proteolytic extract can range from about 0.2 mg/day to about 40 mg/day. In a certain embodiment, the pharmaceutical composition is administered in two or more aliquots, each comprising about 0.5-1.5 mg, optionally in 0.2-0.5 ml of solution or suspension.

In certain embodiments, the organ into which the pharmaceutical composition comprising the proteolytic extract is administered is immobilized for several hours, e.g., 2 to 12 hours.

Each possibility disclosed throughout the specification is a separate embodiment of the invention.

The following examples are presented to provide a more complete understanding of the invention. The specific techniques, conditions, materials, proportions and reported data set forth to illustrate the principles of the invention are exemplary and should not be construed as limiting the scope of the invention.

EXAMPLE 1

The Collagenolytic Activity of the Proteolytic Extract

The proteolytic extract was obtained from bromelain as described in WO 2006/054309.

The ability of two batches of Debrase to degrade collagen type IV was first determined. The assay was based on EnzChek® Gelatinase/colllagenase Assay Kit (Invitrogen) which contained DQ collagen type IV™ labeled with fluorescein as a substrate. This substrate is known to be efficiently digested by collagenases to yield highly fluorescent peptides. The increase in fluorescence is proportional to the proteolytic activity.

To each well, a Debrase reaction buffer (0.15 M Tris-HCl and 10 mM EDTA, pH 7.6) was added in order to obtain a final volume of 100 μL. Ten μL of 0.5 μg/μl of DQ collagen type IV™ solution were then added to the wells. Thereafter, different volumes (10-80 μL) of freshly prepared Debrase at a concentration of 0.225-1 ng/μL were added to the wells in Debrase buffer to achieve concentrations of 1.5-20 ng/well. Debrase buffer was used as a negative control. Reaction plate was incubated at room temperature for 20 minutes. To stop the reaction, 20 μL of stop reaction solution (0.324 mM iodoacetic acid in Debrase buffer) were added. Fluorescence intensity was measured by a fluorescence micro-plate reader (Analyst AD, LJL) equipped with standard fluorescein filters. Background fluorescence from wells incubated in the absence of enzyme was subtracted.

FIG. 1 shows the collagenolytic activity of two batches of Debrase. As shown in the figure, the two batches of Debrase exerted similar collagenolytic activity indicating that the experimental procedure for obtaining the proteolytic extract of the present invention yields consistent enzyme preparations.

Figure 2:
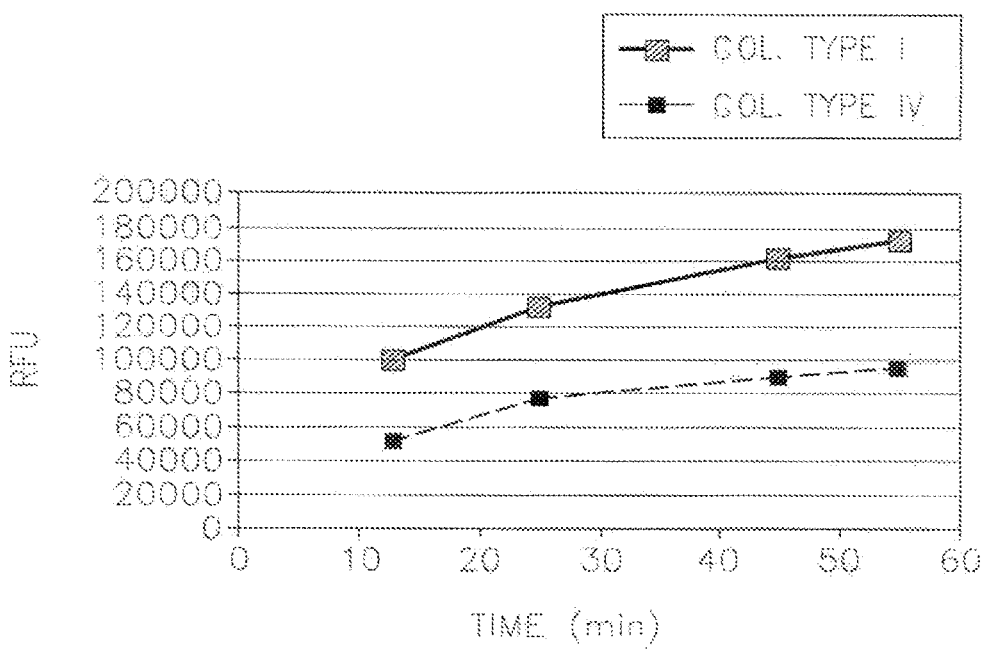
FIG. 2 is a graph showing the collagenolytic activity of the proteolytic extract on collagen type I and type IV. The proteolytic extract was incubated in the presence of fluorescently labeled collagen type I or collagen type IV for various time periods. At the end of the incubation fluorescence was measured. Results are presented in relative fluorescence units (RFU).

Next, the ability of the proteolytic extract to degrade collagen types I and IV was determined. For that end, DQ collagen type IV™ and DQ collagen type I™ labeled with fluorescein were used as substrates. The assay was performed as described herein above and continued for the time periods as indicated in FIG. 2. The reaction was stopped by the addition of 20 μL stop reaction solution (0.324 mM iodoacetic acid in Debrase buffer) and the fluorescence intensity was measured as described herein above.

Collagenase purified from *Clostridium histolyticum* served as a positive control with predefined activity (one unit was defined as the amount of enzyme required to liberate 1 micromole of E-leucine equivalents from collagen in 5 hours at 37° C., pH 7.5).

For the assay with *Clostridium histolyticum* collagenase, a reaction buffer for collagenase (0.05 M Tris-HCl, 0.15 M NaCl, 5 mM CaCl2, 0.2 mM sodium azide, pH 7.6) was added to obtain a final volume of 100 μL per each well.

Then, different volumes (10-80 μL) of *Clostridium* collagenase, 0.4-1 mU/μL, in *Clostridium* collagenase buffer where added to reference wells to reach concentrations ranging from 5 to 80 mU/well. To stop the *Clostridium* collagenase reaction—20 μL of 2 mg/ml 1,10-phenanthroline in collagenase buffer was added.

Data from *Clostridium* collagenase were used as a reference value per mUnit. Data from the proteolytic extract (also named Debrase) samples were divided by the reference value to determine mU/ng Debrase.

FIG. 2 shows that the proteolytic extract degraded collagen type I and IV with a specific activity of 1.58 and 1.27 mU/ng, respectively.

Next, the activity of the proteolytic extract was compared to *Clostridium histolyticum* collagenase activity against collagen. The proteolytic activity of collagenase against gelatin was also measured using the EnzChek® Gelatinase/colllagenase Assay Kit (Invitrogen) and DQ gelatin™ (Invitrogen) as a substrate.

Figure 3:
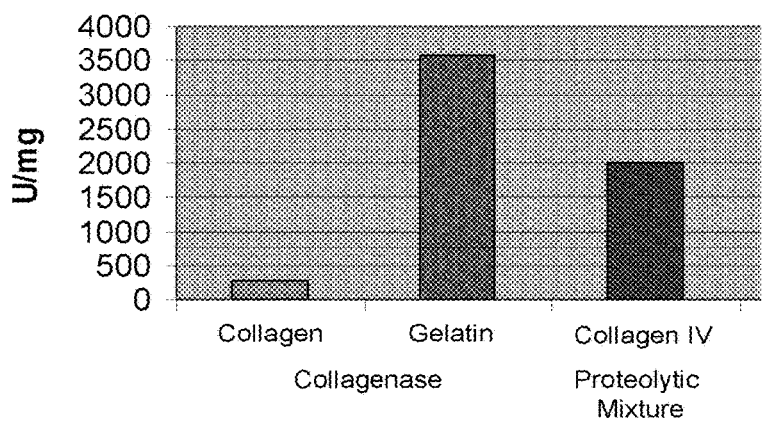
FIG. 3 is a graph showing the collagenolytic activity of the proteolytic extract as compared to that of collagenase. *Clostridium histoliticum* collagenase was incubated with either fluorescently labeled collagen type IV or fluorescently labeled gelatin and fluorescence was measured at the end of 20 minutes of incubation. The proteolytic extract was incubated with fluorescently labeled collagen type IV for 20 minutes and thereafter fluorescence was measured.

FIG. 3 shows that the proteolytic extract exerted collagenolytic activity against collagen type IV, which activity was higher than that obtained by the commercially available collagenase against collagen.

Figure 4:
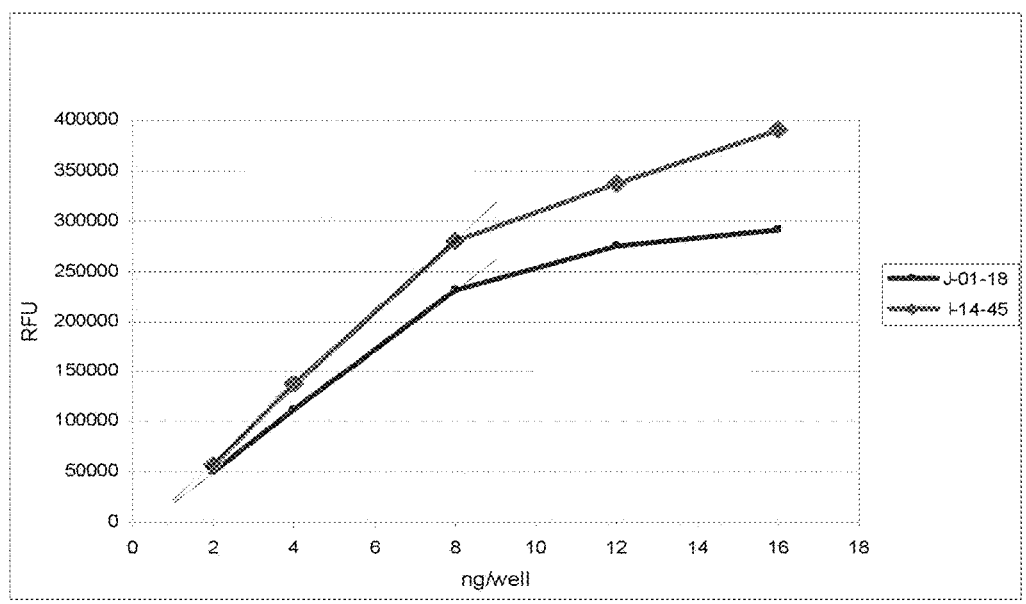
FIG. 4 is a graph showing the gelatinase activity of the proteolytic extract. Increasing concentrations of two batches of the proteolytic extract (designated J-01-19 and J-14-45) were incubated for 20 minutes in the presence of fluorescently labeled gelatin and thereafter fluorescence was measured.

FIG. 4 shows that the proteolytic extract exerted gelatinase activity. As shown in the figure, gelatinase activity of the proteolytic extract was linear at a concentration range of 2-8 ng/well.

EXAMPLE 2

The Proteolytic Extract Facilitates Rupture of Dupuytren's Cord

Figure 5A:
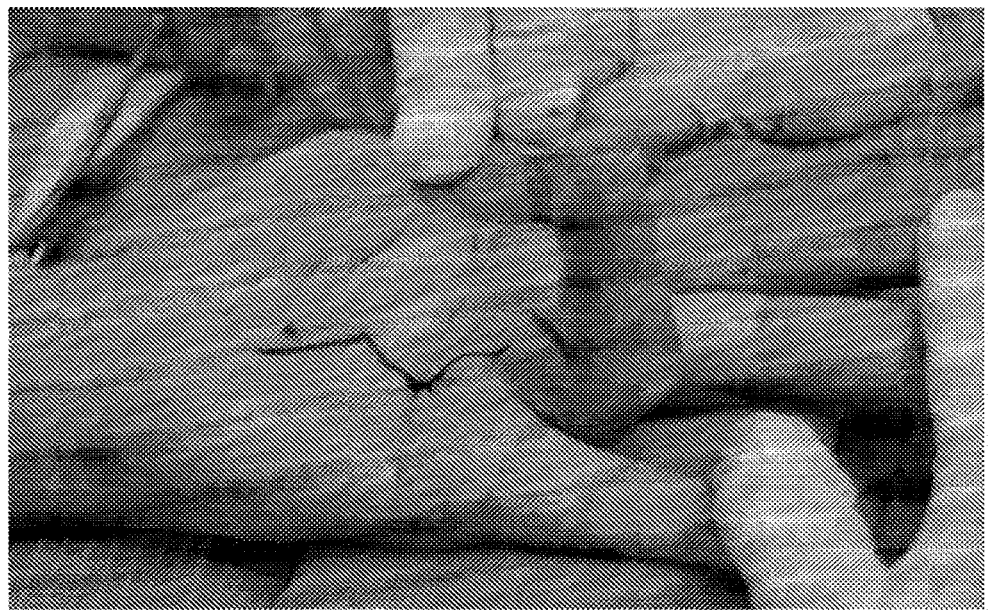
FIGS. 5A-C are photographs showing surgical excision-removal of the Dupuytren's cord from a patient.
Figure 5B:
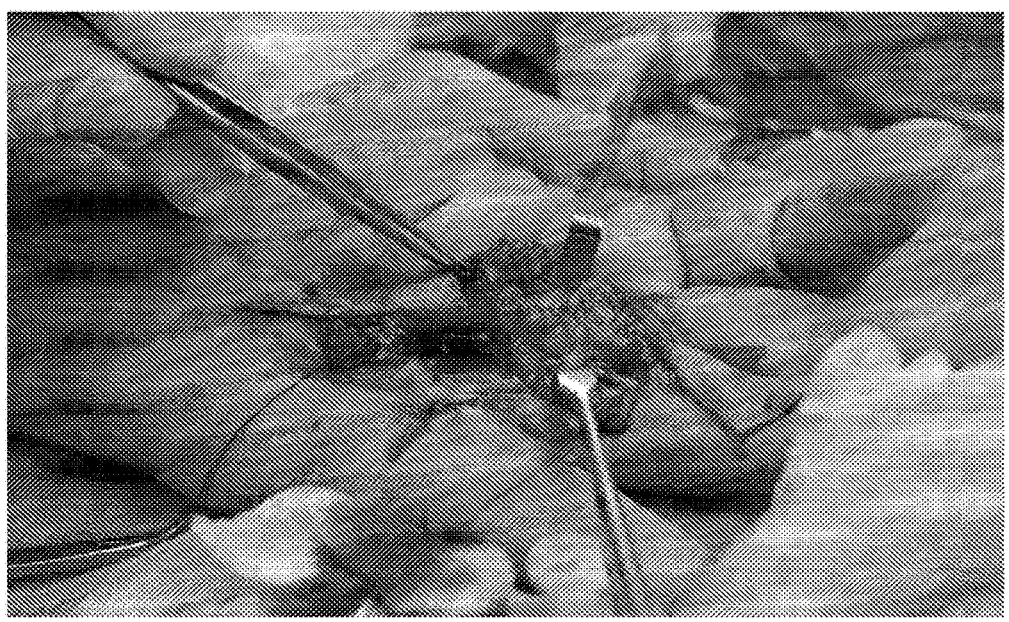
Figure 5C:

Dupuytren's cords were obtained from patients undergoing fasciectomy (FIGS. 5A, 5B and 5C). Consent forms were signed by all subjects prior to surgery and the study was approved by a Helsinki committee. The experiment examined the capability of the proteolytic extract to perform fasiectomy of the cord.

Tissue Preparation

Figure 6:
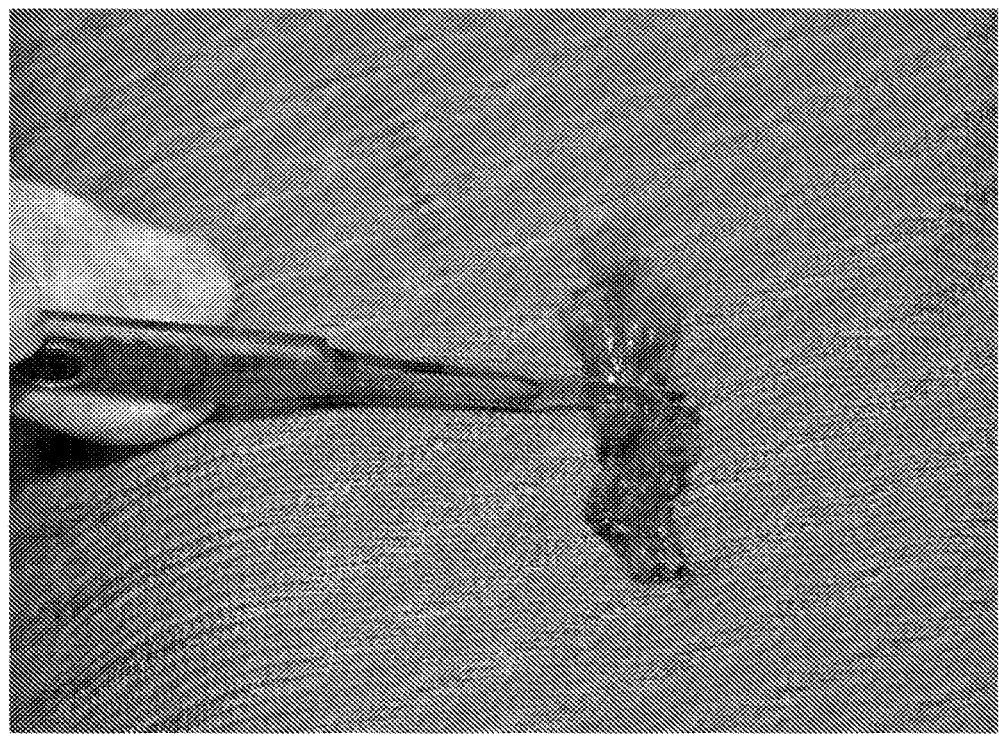
FIG. 6 is a photograph showing the dissection of the Dupuytren's cord to two.
Figure 7:
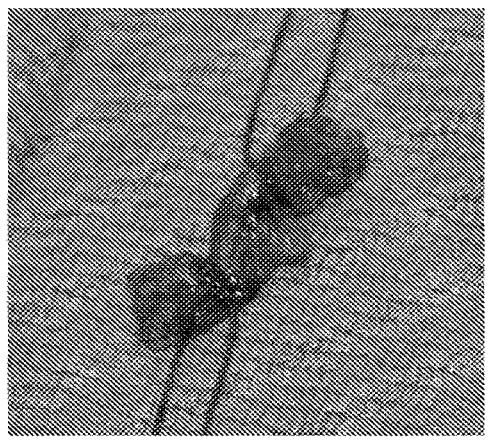
FIG. 7 is a photograph showing the anchoring of the cord.
Figure 8:
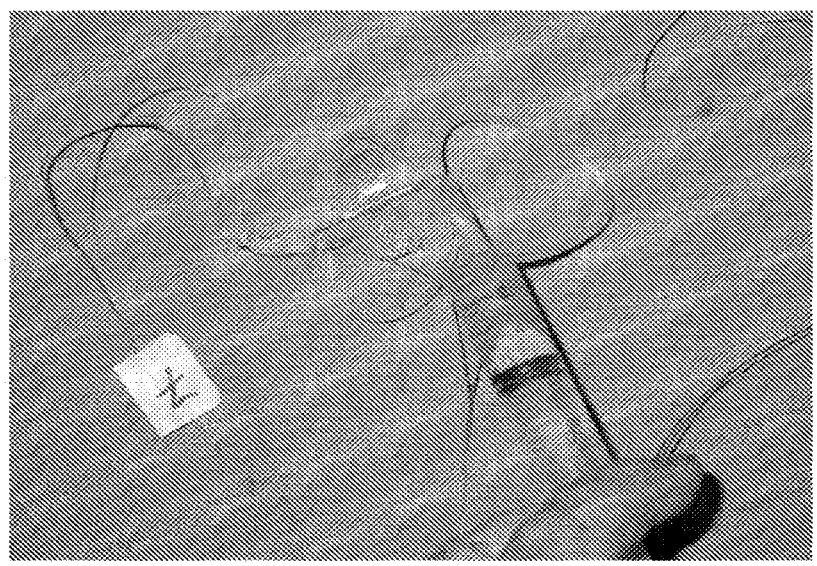
FIG. 8 is a photograph showing the injecting step of a solution into the Dupuytren's cord.
Figure 9:
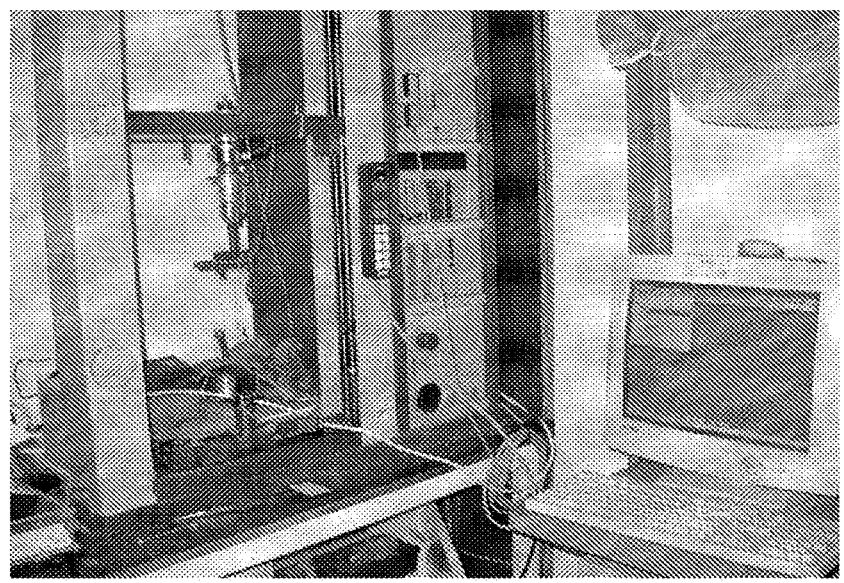
FIG. 9 is a photograph showing the tensile stretching machine.

The cords obtained from the patients were divided to two or three pieces, depending on their length (FIG. 6). The cords were connected by the Krackov technique to a mechanical testing device via a prolene 1 suture (Ethicon, Somerville, N.J.) (FIG. 7). One of the two cords was injected with the proteolytic extract (0.3-0.5 ml of the proteolytic extract according to the cord size) and the second, control cord, was injected with saline (FIG. 8). The cords of the proteolytic extract group were immersed in the proteolytic extract solution and the cords of the control group were immersed in saline. Both groups were incubated at 37° for 24 hours.

Mechanical Testing

After 24 hours of incubation, all cords were connected to a mechanical tensile stress testing device (Zwick 1445 testing system, Zwick Co., Germany). Each cord was subjected to an increasing load until the cord or the connecting suture was ruptured. The device measured the applied tensile force until rupture.

Histological Analysis

A sample of each specimen was obtained for histological analysis and for determination of the disease stage.

Statistical Analysis

The efficiency of the control group compared to the study group was tested using Fisher exact test.

Results

Figure 10A:
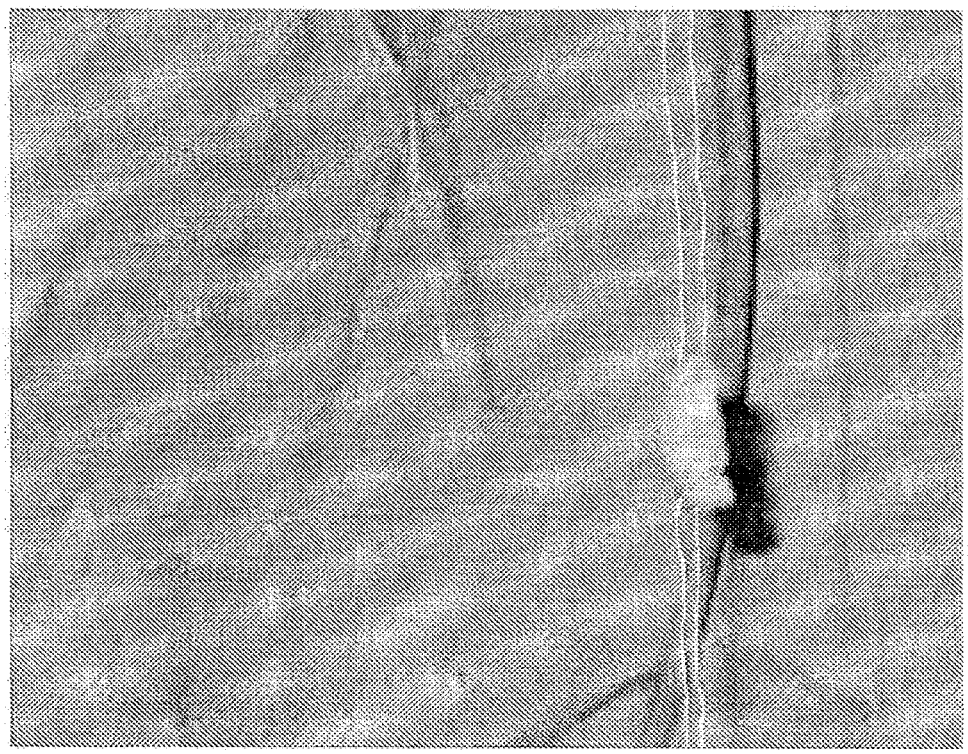
FIGS. 10A-B are photographs showing the cord before and after tensile force application.
Figure 10B:
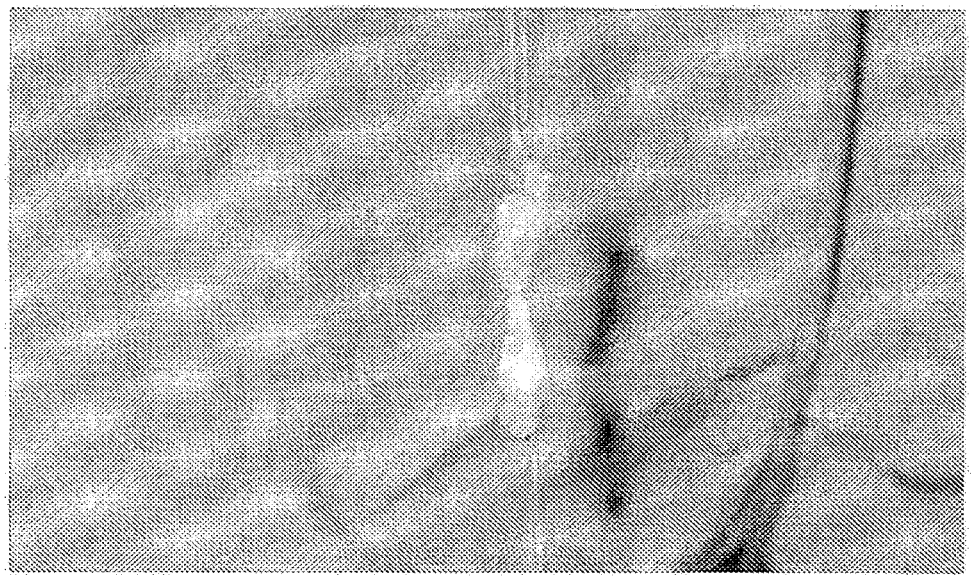
Figure 11:
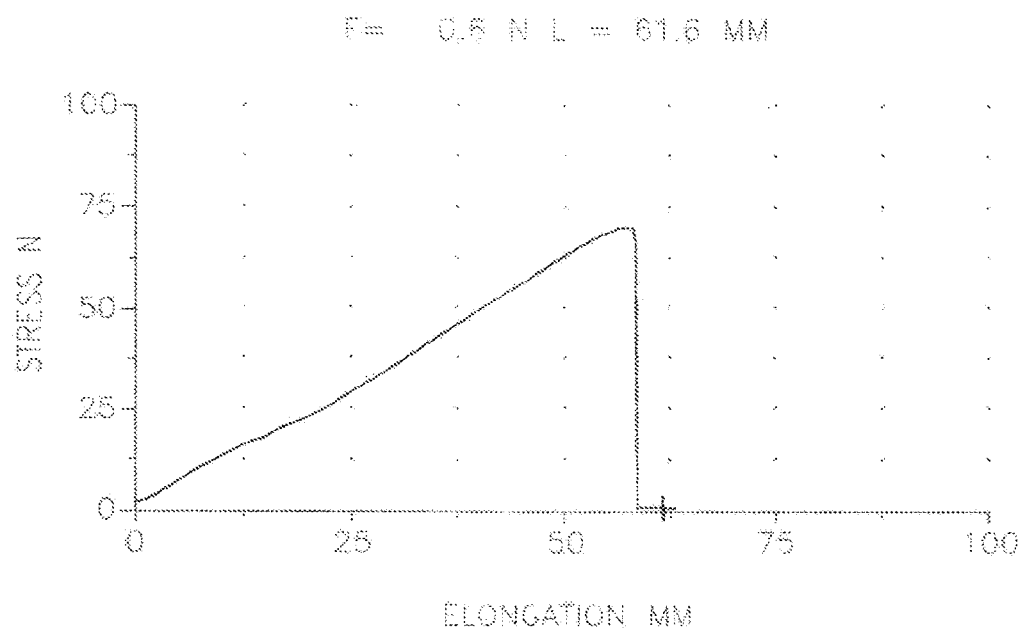
FIG. 11 shows the effect of saline on Dupuytren's cord elongation as a function of tensile strength application. Dupuytren's cord was injected with saline and incubated in saline for 24 hours. Thereafter, the cord was subjected to tensile stress, and cord elongation and rupture was evaluated.
Figure 12:
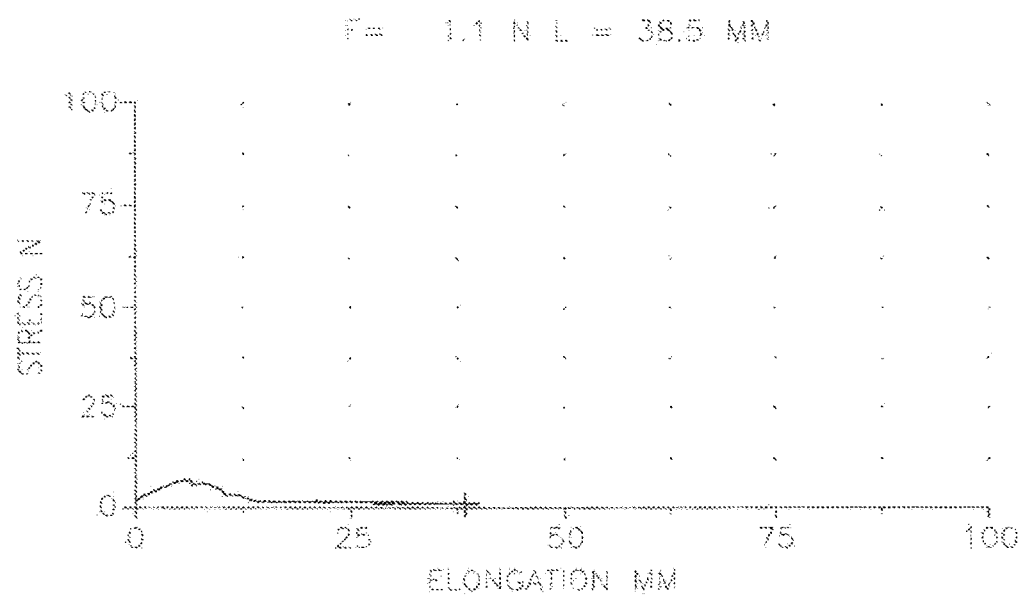
FIG. 12 shows the effect of the proteolytic extract on Dupuytren's cord elongation as a function of tensile strength application. Dupuytren's cord was injected with the proteolytic extract and incubated in the presence of the proteolytic extract for 24 hours. Thereafter, the cord was subjected to tensile stress, and cord elongation and rupture was evaluated.

All the cords treated with the proteolytic extract (n=10) were ruptured following stretching (FIGS. 10A and 10B). Some of the cords treated with the proteolytic extract were almost completely ruptured, practically dissolved prior to the mechanical test. All control cords (n=9) did not rupture following the tensile force application. As depicted in FIG. 11, all the control cords exhibited a similar stress elongation pattern represented by a limited elongation with increasing stress of the cord until ruptured when a very high load applied. In contrast, all the cords treated with the proteolytic extract exhibited loss of the cord's tensile strength, culminating in rupture of the cord at a very low stress (FIG. 12). The results demonstrated that low doses, i.e., 0.8 mg/ml, of the proteolytic extract were capable of rupturing the Dupuytren's diseases cords and that this effect was further demonstrated at higher doses of the proteolytic extract, i.e., up to 150 mg/ml.

In order to evaluate the effect of a single injection of the proteolytic extract on the stretching of Dupuytren's cord, the cords were injected with the proteolytic extract at three different sites along the cord and then incubated in saline in the absence of the proteolytic extract for 24 hours at 37° C.

Figure 13:
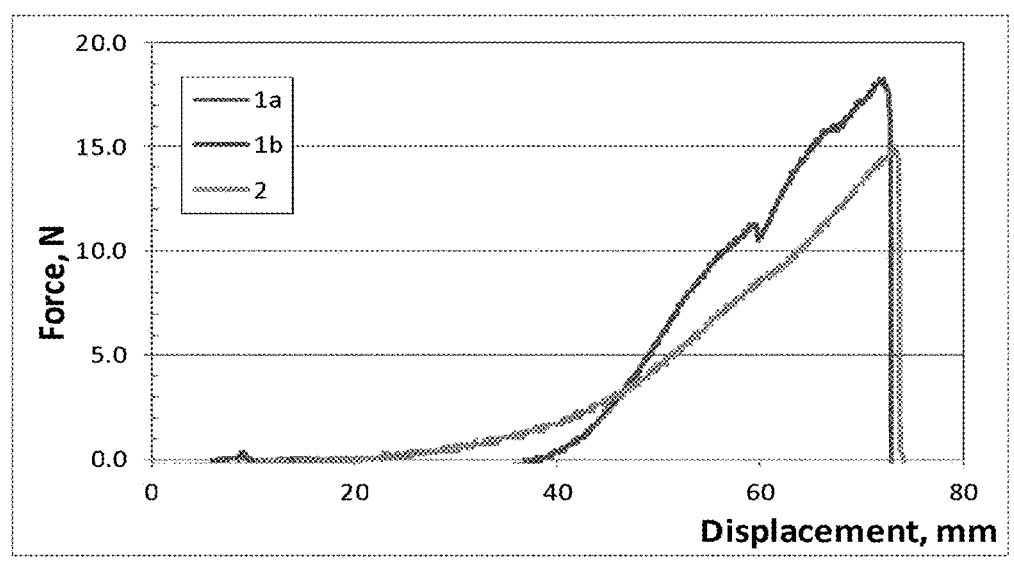
FIG. 13 shows the effect of a single injection of the proteolytic extract on Dupuytren's cord elongation as a function of tensile strength application. Dupuytren's cords were injected with the proteolytic extract and incubated in saline for 24 hours. Thereafter, the cords were subjected to tensile stress, and cord elongation and rupture were evaluated.

FIG. 13 shows that injections of the proteolytic extract given at three sites of the Dupuytren's cords were capable of reducing the tensile strength of the cords by a factor of 4-5 (see FIG. 13, test 1a and 2 showing cord rupture at a stress of 18 N and 15 N, respectively 13). One cord (FIG. 13, test 1b) underwent rupture at a stress of 0.4 N. These results demonstrate the efficiency of the proteolytic extract to dissolve Dupuytren's cords and clearly imply that the proteolytic extract of the present invention is a highly effective enzymatic medication for Dupuytren's disease as well as for other connective tissue diseases involving excess collagen deposition.

It will be appreciated by persons skilled in the art that the present invention is not limited by what has been particularly shown and described herein above. Rather the scope of the invention is defined by the claims that follow.

What is claimed is:

1. A method of treating a connective tissue disease comprising injecting into a subject in need of such treatment a pharmaceutical composition comprising a therapeutically effective amount of a proteolytic extract obtained from bromelain and a pharmaceutically acceptable carrier, wherein the proteolytic extract comprises stem bromelain EC 3.4.22.32, ananain EC 3.4.22.31, at least one cysteine protease precursor, at least one cysteine protease fragment, and a lectin, wherein the connective tissue disease is associated with excess collagen deposition, and wherein the step of injecting is repeated two or more times.

2. The method according to claim 1, wherein the connective tissue disease is selected from the group consisting of Dupuytren's disease, Peyronie's disease, frozen shoulder, and Ledderhose disease.

3. The method according to claim 1, wherein the connective tissue disease is Dupuytren's disease.

4. The method according to claim 1, wherein the connective tissue disease is Peyronie's disease.

5. The method according to claim 1, wherein the pharmaceutical composition further comprises an agent selected from the group consisting of an anesthetic agent, an antibacterial agent, and an anti-inflammatory agent.

6. The method according to claim 5, wherein the anesthetic agent is selected from the group consisting of amethocaine (tetracaine), lignocaine (lidocaine), xylocaine, bupivacaine, prilocaine, ropivacaine, benzocaine, mepivocaine, cocaine and combinations thereof.

7. The method according to claim 5, wherein the antibacterial agent is selected from the group consisting of amanfadine hydrochloride, amanfadine sulfate, amikacin, amikacin sulfate, amoglycosides, amoxicillin, ampicillin, amsamycins, bacitracin, beta-lactams, candicidin, capreomycin, carbenicillin, cephalexin, cephaloridine, cephalothin, cefazolin, cephapirin, cephradine, cephaloglycin, chilomphenicols, chlorhexidine, chloshexidine gluconate, chlorhexidine hydrochloride, chloroxine, chlorquiraldol, chlortetracycline, chlortetracycline hydrochloride, ciprofloxacin, circulin, clindamycin, clindamycin hydrochloride, clotrimazole, cloxacillin, demeclocycline, diclosxacillin, diiodohydroxyquin, doxycycline, ethambutol, ethambutol hydrochloride, erythromycin, erythromycin estolate, erhmycin stearate, farnesol, floxacillin, gentamicin, gentamicin sulfate, gramicidin, giseofulvin, haloprogin, haloquinol, hexachlorophene, iminocylcline, iodochlorhydroxyquin, kanamycin, kanamycin sulfate, lincomycin, lineomycin, lineomycin hydrochloride, macrolides, meclocycline, methacycline, methacycline hydrochloride, methenine, methenamine hippurate, methenamine mandelate, methicillin, metonidazole, miconazole, miconazole hydrochloride, minocycline, minocycline hydrochloride, mupirocin, nafcillin, neomycin, neomycin sulfate, netimicin, netilmicin sulfate, nitrofurazone, norfloxacin, nystatin, octopirox, oleandomycin, orcephalosporins, oxacillin, oxyteacline, oxytetracycline hydrochloride, parachlorometa xylenol, paromomycin, paromomycin sulfate, penicillins, penicillin G, penicillin V, pentamidine, pentamidine hydrochloride, phenethicillin, polymyxins, quinolones, streptomycin sulfate, tetracycline, tobramycin, tolnaftate, triclosan, trifampin, rifamycin, rolitetracycline, silver salts, spectinomycin, spiramycin, struptomycin, sulfonamide, tetracyclines, tetracycline, tobramycin, tobramycin sulfate, triclocarbon, triclosan, trimethoprim-sulfamethoxazole, tylosin, vancomycin, and yrothricin.

8. The method according to claim 5, wherein the anti-inflammatory agent is selected from the group consisting of non-steroidal anti-inflammatory agents, and steroidal anti-inflammatory agents.

9. The method of claim 1, wherein the pharmaceutical composition further comprises a component selected from the group consisting of a stabilizing agent, an anti-oxidant, a preservative, a buffering agent, a chelating agent, and a tonicity agent.

10. The method according to claim 1, wherein the pharmaceutical composition is formulated in a form selected from the group consisting of a solid formulation, a semi solid formulation, a liquid formulation, and a foam formulation.

11. The method according to claim 10, wherein the solid formulation is a powder.

12. The method according to claim 10, wherein the liquid formulation has a pH of about 6 to about 7.

13. The method according to claim 1, wherein the pharmaceutical composition is injected into the diseased fibrous tissue.

14. The method according to claim 1, wherein the connective tissue disease associated with excess collagen deposition is selected from the group consisting of fibrous tissue malformations and fibrous tissue abnormalities.

15. The method according to claim 14, wherein the fibrous tissue malformations and fibrous tissue abnormalities are selected from the group consisting of fibrosis of joint capsules, fibrosis of tendons, fibrosis of ligament sheaths, and fibrosis of skin or within skin.

16. The method according to claim 1, wherein the proteolytic extract comprises stem bromelain EC 3.4.22.32, ananain EC 3.4.22.31, at least one cysteine protease precursor, at least one cysteine protease fragment, and a lectin, wherein the connective tissue disease is Dupuytern's disease, and wherein the pharmaceutical composition further comprises an anesthetic agent.

17. The method according to claim 16, wherein the anesthetic agent is lignocaine (lidocaine), and wherein the pharmaceutical composition further comprises a buffering agent which is monobasic sodium phosphate and dibasic sodium phosphate.

\* \* \* \* \*